United States Patent
Branch et al.

(10) Patent No.: US 6,945,933 B2
(45) Date of Patent: Sep. 20, 2005

(54) INSTRUMENTS AND METHODS FOR MINIMALLY INVASIVE TISSUE RETRACTION AND SURGERY

(75) Inventors: Charles L. Branch, Advance, NC (US); Kevin T. Foley, Germantown, TN (US); Thomas E. Roehm, III, Braden, TN (US); Anthony J. Melkent, Germantown, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 92 days.

(21) Appl. No.: 10/180,658

(22) Filed: Jun. 26, 2002

(65) Prior Publication Data

US 2004/0002629 A1 Jan. 1, 2004

(51) Int. Cl.[7] .................................. A61B 1/32
(52) U.S. Cl. ................. 600/210; 600/214; 600/215; 600/233
(58) Field of Search ................. 600/114, 232, 600/233, 210, 213, 214, 235, 215, 205, 201, 218, 221, 224, 219, 206, 207, 208; 606/119, 197, 198, 96, 206, 207

(56) References Cited

U.S. PATENT DOCUMENTS 563,236 A * 6/1896 Penhall ...................... 600/220
1,400,616 A 12/1921 McCrory
2,661,735 A 12/1953 Darden
3,054,398 A * 9/1962 Kobler ....................... 600/206
3,752,149 A 8/1973 Ungar et al.

(Continued)

FOREIGN PATENT DOCUMENTS

| DE | 87 04 901 U | 7/1987 |
|---|---|---|
| EP | 1 192 905 | 9/2001 |
| FR | 1 019 217 A | 1/1952 |
| FR | 2 788 958 | 8/2000 |
| FR | 2 807 313 | 10/2001 |

OTHER PUBLICATIONS

U.S. Appl. No. 10/720,656, filed Nov. 24, 2003, Frey et al.

Primary Examiner—Pedro Philogene
(74) Attorney, Agent, or Firm—Krieg DeVault LLP

(57) ABSTRACT

Methods and devices retract tissue for minimally invasive surgery in a patient. A retractor includes a working channel formed by a first portion and a second portion. The first and second portions are movable relative to one another from a first configuration for insertion that minimizes trauma to skin and tissue to an enlarged configuration after insertion to further retract skin and tissue in a minimally invasive manner. Instruments are engageable to the first and second portions and operable to move the first and second portions relative to one another.

76 Claims, 7 Drawing Sheets

U.S. PATENT DOCUMENTS

| | | | | |
|---|---|---|---|---|
| 3,788,318 A | | 1/1974 | Kim et al. | |
| 4,263,899 A | * | 4/1981 | Burgin | 600/213 |
| 4,545,374 A | | 10/1985 | Jacobson | |
| 4,716,901 A | | 1/1988 | Jackson et al. | |
| 4,747,394 A | | 5/1988 | Watanabe | |
| 4,765,311 A | | 8/1988 | Kulik et al. | |
| 4,817,587 A | | 4/1989 | Janese | |
| 4,899,729 A | | 2/1990 | Gill et al. | |
| 5,125,396 A | * | 6/1992 | Ray | 600/208 |
| 5,139,511 A | | 8/1992 | Gill et al. | |
| 5,158,545 A | | 10/1992 | Trudell et al. | |
| 5,163,949 A | | 11/1992 | Bonutti | |
| 5,197,971 A | | 3/1993 | Bonutti | |
| 5,312,417 A | | 5/1994 | Wilk | |
| 5,339,803 A | | 8/1994 | Mayzels et al. | |
| 5,353,784 A | | 10/1994 | Nady-Mohamed | |
| 5,389,080 A | | 2/1995 | Yoon | |
| 5,490,819 A | | 2/1996 | Nicholas et al. | |
| 5,509,893 A | * | 4/1996 | Pracas | 600/224 |
| 5,512,038 A | | 4/1996 | O'Neal et al. | |
| 5,549,595 A | | 8/1996 | Freitas | |
| 5,573,517 A | | 11/1996 | Bonutti et al. | |
| 5,674,240 A | | 10/1997 | Bonutti et al. | |
| 5,681,265 A | * | 10/1997 | Maeda et al. | 600/219 |
| 5,707,359 A | | 1/1998 | Bufalini | |
| 5,755,732 A | | 5/1998 | Green et al. | |
| 5,785,648 A | * | 7/1998 | Min | 600/206 |
| 5,823,947 A | | 10/1998 | Yoon et al. | |
| 5,888,196 A | | 3/1999 | Bonutti | |
| 5,928,139 A | * | 7/1999 | Koros et al. | 600/205 |
| 5,944,658 A | | 8/1999 | Koros et al. | |
| 5,951,466 A | | 9/1999 | Segermark et al. | |
| 5,961,499 A | | 10/1999 | Bonutti et al. | |
| 5,976,146 A | | 11/1999 | Ogawa et al. | |
| 6,027,518 A | | 2/2000 | Gaber | |
| 6,042,540 A | | 3/2000 | Johnston et al. | |
| 6,074,380 A | | 6/2000 | Byrne et al. | |
| 6,083,154 A | | 7/2000 | Liu et al. | |
| 6,096,046 A | * | 8/2000 | Weiss | 606/119 |
| 6,099,547 A | | 8/2000 | Gellman et al. | |
| 6,139,493 A | | 10/2000 | Koros et al. | |
| 6,149,583 A | * | 11/2000 | Vierra et al. | 600/204 |
| 6,162,236 A | | 12/2000 | Osada | |
| 6,171,299 B1 | | 1/2001 | Bonutti | |
| 6,187,000 B1 | | 2/2001 | Davison et al. | |
| 6,200,322 B1 | | 3/2001 | Branch et al. | |
| 6,224,545 B1 | * | 5/2001 | Cocchia et al. | 600/233 |
| 6,296,609 B1 | | 10/2001 | Brau | |
| 6,312,443 B1 | | 11/2001 | Stone | |
| 6,325,812 B1 | | 12/2001 | Dubrul et al. | |
| 6,361,492 B1 | | 3/2002 | Santilli | |
| 6,371,911 B1 | | 4/2002 | Hossain et al. | |
| 6,450,952 B1 | * | 9/2002 | Rioux et al. | 600/223 |

\* cited by examiner

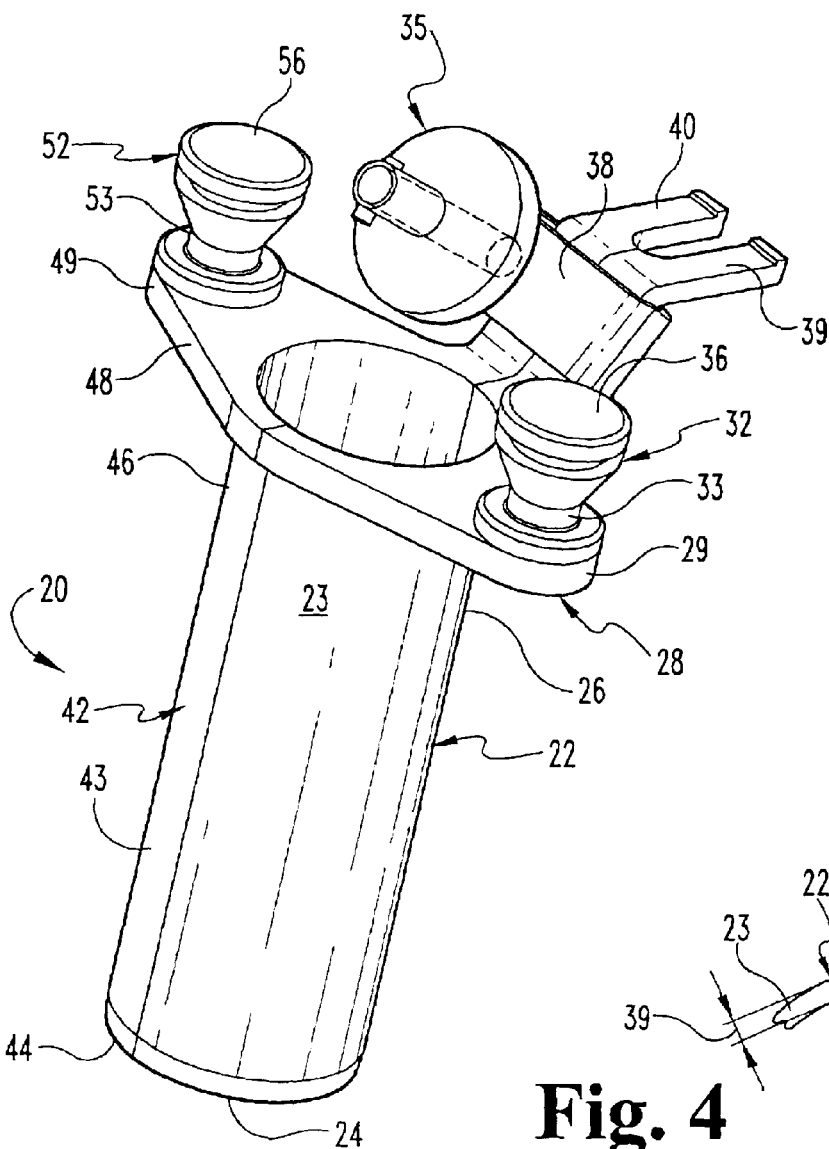
Fig. 3
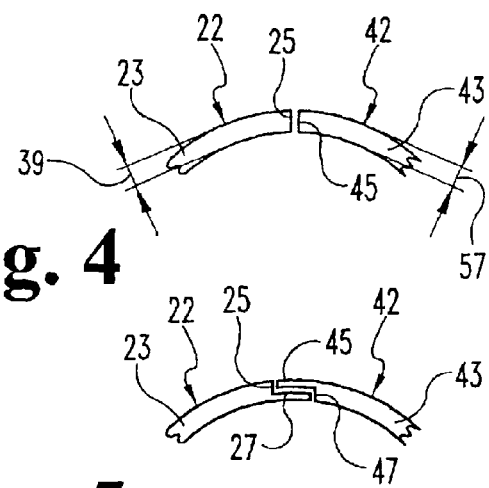
Fig. 4
Fig. 5
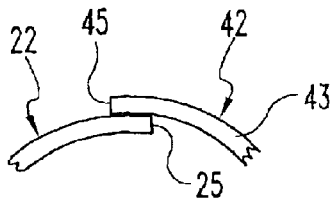
Fig. 6

US 6,945,933 B2

INSTRUMENTS AND METHODS FOR MINIMALLY INVASIVE TISSUE RETRACTION AND SURGERY

BACKGROUND

The present invention relates to instruments and methods for performing tissue retraction and surgeries through the retracted tissue in minimally invasive procedures.

Traditional surgical procedures for pathologies located within the body can cause significant trauma to the intervening tissues. These procedures often require a long incision, extensive muscle stripping, prolonged retraction of tissues, denervation and devascularization of tissue. These procedures can require operating room time of several hours and several weeks of post-operative recovery time due to the destruction of tissue during the surgical procedure. In some cases, these invasive procedures lead to permanent scarring and pain that can be more severe than the pain leading to the surgical intervention.

The development of percutaneous procedures has yielded a major improvement in reducing recovery time and post-operative pain because minimal dissection of tissue, such as muscle tissue, is required. For example, minimally invasive surgical techniques are desirable for spinal and neurosurgical applications because of the need for access to locations within the body and the danger of damage to vital intervening tissues. While developments in minimally invasive surgery are steps in the right direction, there remains a need for further development in minimally invasive surgical instruments and methods.

SUMMARY

The present invention is directed to methods and instruments for performing surgery in a patient. One specific application concerns instruments and methods for tissue retraction in minimally invasive spinal surgery. A further specific application includes instruments for percutaneous tissue retraction to provide access to a surgical location in the patient. Another specific application includes surgical methods performed through the percutaneously retracted tissue at any location in a patient's body. Other applications of the invention will also be apparent from the following description of the illustrated embodiments.

BRIEF DESCRIPTION OF THE FIGURES

FIG. 3 is a perspective of another embodiment retractor in an insertion configuration.

FIG. 4 is a detailed view of one configuration of adjacent retractor portions in an insertion configuration.

FIG. 5 is a detailed view of another configuration of adjacent retractor portions in an insertion configuration.

FIG. 6 is a detailed view of another configuration of adjacent retractor portions in an insertion configuration.

DESCRIPTION OF THE ILLUSTRATED EMBODIMENTS

Figure 1:
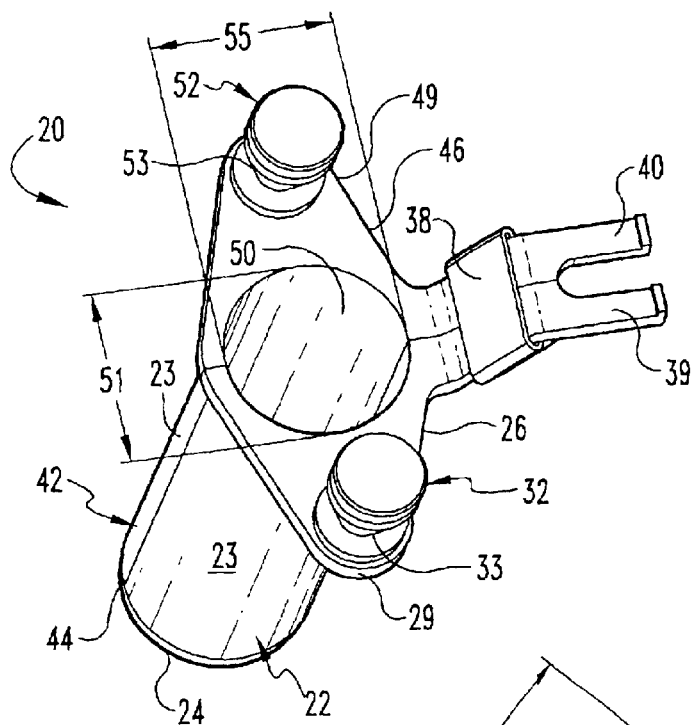
FIG. 1 is a perspective view of one embodiment retractor in an insertion configuration.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices and described methods, and any such further applications of the principles of the invention as illustrated herein are contemplated as would normally occur to one skilled in the art to which the invention relates.

The present invention provides instruments and methods for performing percutaneous surgery, including spinal surgeries that include one or more techniques such as laminotomy, laminectomy, foramenotomy, facetectomy, discectomy, interbody fusion, spinal nucleus or disc replacement, and implant insertion, for example. The surgery is performed through a working channel or passageway through skin and tissue of the patient provided by a retractor. Viewing of the surgical site at the working end of the retractor can be accomplished with viewing instruments mounted on the retractor, positioned over the retractor, and/or through a viewing system such as lateral fluoroscopy. The retractor is movable in situ to increase the size of the working channel to facilitate access to the working space at the distal end of the retractor while minimizing trauma to tissue surrounding the retractor. The retractor can be used with any surgical approach to the spine, including anterior, posterior, posterior mid-line, lateral, postero-lateral, and/or antero-lateral approaches, and in other regions besides the spine.

In FIG. 1 there is illustrated a retractor 20 that includes a first portion 22 and a second portion 42. First portion 22 has a distal end 24 and an opposite proximal end 26. Second portion 42 has a distal end 44 and an opposite proximal end 46. Distal ends 24, 44 can be beveled to facilitate insertion, although non-beveled ends are also contemplated. First portion 22 can be positioned adjacent to or mated with second portion 42 along adjacent ones of the longitudinal edges 25 of first portion 22 and longitudinal edges 45 of second portion 42. A working channel 50 is formed between first portion 22 and second portion 42. Working channel 50 extends between and opens at distal ends 24, 44 and proximal ends 26, 46.

Retractor 20 is insertable through skin and tissue of a patient to provide working channel 50 to the surgical site. It is contemplated that retractor 20 is inserted through the skin and tissue in an insertion configuration for working channel 50, such as shown in FIG. 1. In the insertion configuration, working channel 50 is substantially enclosed or circumscribed by first portion 22 and second portion 42. After insertion into the patient, working channel 50 can be enlarged by separating first portion 22 and second portion 42. Separation of first and second portions 22, 42 increases the size of working channel 50 from proximal ends 26, 46 to distal ends 24, 44.

In the insertion configuration of FIG. 1, working channel 50 is circumscribed or substantially enclosed by first portion 22 and second portion 42. Working channel 50 can have a size in the insertion configuration that allows passage of one or more surgical instruments and/or implants to the surgical location in the patient's body. It may be desirable during surgery to provide greater access to the location in the patient's body beyond the locations provided through working channel 50 in its insertion configuration. First portion 22 and second portion 42 are movable away from one another to enlarge working channel 50. In the enlarged configuration of working channel 50, a space is formed between at least of the adjacent longitudinal edges 25, 45 of first and second portions 22, 42. The space between the adjacent longitudinal edges 25, 45 exposes enlarged working channel 50 to skin and tissue of the patient between the separated first portion 22 and second portion 42. This exposed tissue can also be accessed by the surgeon through the enlarged working channel 50 with one or more instruments and/or implants. It is further contemplated that a shield, guard or tissue retractor could be placed in enlarged working channel 50 to maintain the exposed tissue away from the enlarged working channel 50.

First portion 22 includes a semi-cylindrical body 23 extending between distal end 24 and proximal end 26. A collar 28 extends about proximal end 26, and forms a lip extending about the outer surface of body 23. First portion 22 includes a first bracket member 39 extending from proximal end 26. Second portion 42 includes a semi-cylindrical body 43 extending between distal end 44 and proximal end 46. A collar 48 extends about proximal end 46 of second portion 42, and defines a lip extending about the outer surface of body 43. Second portion 42 includes a second bracket member 40 extending from proximal end 46.

A first alignment member 30 can be provided to couple a first side of first portion 22 to second portion 42 adjacent proximal ends 26, 46. A second alignment member 31 opposite first alignment member 30 can be provided to couple the other side of first portion 22 to second portion 42 adjacent proximal ends 26, 46 along another side of retractor 20. Holding member 38 can be positioned about bracket members 39, 40 to hold first portion 22 and second portion 42 adjacent one another. In one embodiment, alignment members 30, 31 are pins slidably received in holes 43 (only one shown in FIG. 2) formed in the other retractor portion when retractor 20 is in its insertion configuration. Alignment members 30, 31 maintain first portion 22 and second portion 42 in longitudinal alignment with one another during and after insertion. Holding member 38 can be resiliently biased to engage bracket members 39, 40 and maintain first portion 22 and second portion 42 adjacent one another during and after insertion. Holding member 38 can be removed from bracket members 39, 40 when it is desired to separate first and second portions 22, 42.

Other arrangements are also contemplated for aligning and releasably coupling first portion 22 and second portion 42 to one another. Examples of such arrangements include dovetail connections, fasteners, threaded coupling members, clamping members, snap rings, compression bands, straps, ball-detent mechanisms, and releasably interlocking cams or tabs, for example. Examples of suitable holding members include clamps, clips, bands, straps, hooks, ties, sleeves, coupling members and/or fasteners. As shown in FIG. 3, holding member 38 can be provided with a clamping mechanism 35 to bias holding member 38 into engagement with bracket members 39, 40. Clamping mechanism 35 can include a thumb wheel and threaded shaft that bears against one or both of the bracket members 39, 40 to solidly attach holding member 38 thereto and provide a quick disconnect of holding member 38 from bracket members 39, 40.

Figure 7:
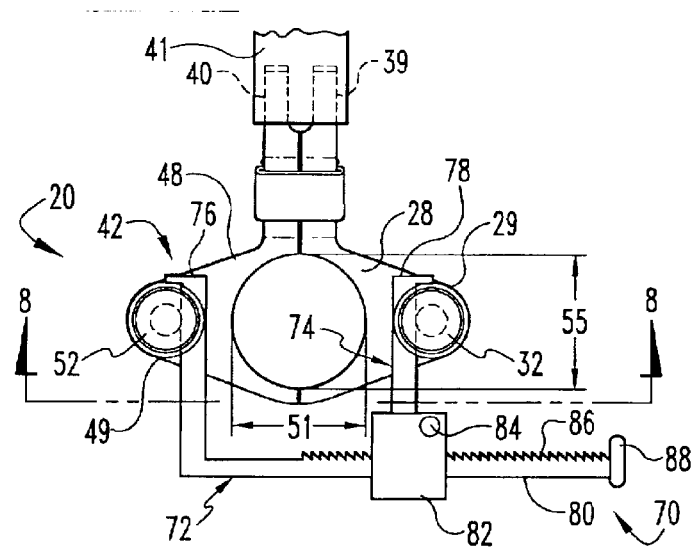
FIG. 7 is a plan view of the retractor of FIG. 1 in an insertion configuration with an instrument for separating first and second portions of the retractor coupled thereto.

Bracket member 39 and 40 can extend from and be integrally formed with or attached to respective ones of the collars 28, 48 of first and second portions 22, 42. Bracket members 39, 40 can also be provided as a single bracket on one of the collars 28, 48 in lieu of or in addition to bracket members 39, 40. Bracket members 39, 40 extend away from working channel 50 and are connectable to one end of a flexible or articulatable arm 41 (FIG. 7.) The opposite end of arm 41 (not shown) can be mounted on the surgical table or other support device. Arm 41 supports retractor 20 in the patient yet allows percutaneous manipulation and re-positioning of retractor 20 during surgery. It is further contemplated that more than one flexible arm 41 can be provided to engage respective ones of the retractor portions 22, 42 after enlargement of working channel 50.

With working channel 50 of retractor 20 in its insertion configuration, the opposite edges 25 of first portion 22 are adjacent respective ones of the opposite edges 45 of second portion 42. Various interfaces between the edges 25, 45 are contemplated. For example, in FIG. 4 there is shown a configuration in which edges 25 (only one shown) of first portion 22 abut along all or a portion of the adjacent edge 45 of second portion 42 in the insertion configuration for working channel 50. In FIG. 5 there is another embodiment first portion 22 having an outer recess 27 along each of the edges 25 (only one shown.) Each of the edges 45 can include an inner recess 47. Edges 25, 45 can thus interdigitate and abut one another in recesses 27, 47 in the insertion configuration for working channel 50. In FIG. 6 there is shown an overlapping arrangement in which edges 25 (only one shown) of first portion 22 can be located inside, relative to working channel 50, the adjacent edge 45 of second portion 42. It is also contemplated that edge 45 could be located inside edge 25. It is further contemplated that on one side of retractor 20 edge 25 can be inside edge 45, and on the other side of retractor 20 the other edge 45 can be inside the other edge 25. Other arrangements contemplate a gap between adjacent ones of the edges 25, 45.

Body 23 has a perimeter length along distal end 24 which can be about the same as the perimeter length of body 23 at proximal end 26. Body 43 of second portion 42 includes a perimeter length along distal end 44 which can be about the same as the perimeter length of body 43 adjacent proximal end 46. Bodies 23, 43 can have a semi-circular cross-section, and form a generally circular cross-section for working channel when placed adjacent one another, as shown in FIG. 1. Other cross-sectional shapes are also contemplated for first and second portions 22, 42, such as, for example, any open sided polygonal shape, curved shape, or combined curved/polygonal shape.

Extending proximally from collar 28 of first portion 22 is a first engagement member 32 having a head portion 36 forming a recess 33 therebelow. Extending proximally from collar 48 of second portion 42 is a second engagement member 52 having a head portion 56 forming a recess 53 therebelow. Head portions 36, 56 can be threadingly engaged, reciprocally engaged and spring biased toward collars 28, 48, or otherwise engaged to the respective collar 28, 48 and adjustable to increase and decrease the height of the respective recess 33, 53 to receive and couple a separation instrument therein. It is also contemplated that engagement members 32, 52 can be non-adjustable, and the separation instrument configured to engage the adjacent engagement member 32, 52.

As discussed further below, an instrument for separating first portion 22 and second portion 42 can be non-releasably or releasably engaged to engagement members 32, 52 for application of a separation force to enlarge working channel 50 by separating first portion 22 and second portion 42. Such an instrument could also be releasable or non-releasably engaged to first portion 22 and second portion 42. Such an instrument could also maintain first portion 22 and second portion 42 in the initial insertion configuration and/or in the enlarged configuration for working channel 50. Other means besides the separation instrument could also be employed for maintaining first portion 22 and second portion 42 in one or both of the initial insertion configuration and the enlarged configuration for working channel 50. For example, when the separation instrument is not attached, a member could extend between and be coupled to each of the engagement members 32, 52 and/or retractor portions 22, 42.

Engagement members 32, 52 are positioned on lateral extensions 29, 49 of collars 28, 48, respectively. Lateral extensions 29, 49 extend far enough laterally to allow engagement of a separation instrument to engagement members 32, 52 without obstructing working channel 50 with the separation instrument.

It is contemplated that body 23 can be provided with a thickness 39 (FIG. 4.) Body 43 of second portion 42 can be provided with a thickness 59 (FIG. 4) that can be the same, greater than, or less than thickness 39 of first portion 22. Bodies 23, 43 can be provided with sufficient rigidity between their distal and proximal ends to separate and maintain separation of body tissue when retractor is initially inserted and also when tissue is retracted by moving first portion 22 and second portion 42 away from one another. First thickness 39 and second thickness 59 can provide first portion 22 and second portion 42, respectively, with sufficient rigidity to resist bending or bowing under the forces exerted on it by the retracted tissue. Also, body 23 has a depth 37 from edges 25 to the midpoint of wall of body 23 extending between edges 25. Depth 37 can provide a sufficient section modulus or moment of inertia in the direction of movement of first portion 22 to resist bending, bowing and/or deflection forces applied during such movement. Similarly, body 43 can have a depth 57 from edges 45 to the midpoint of wall of body 43 extending between edges 45 to provide a sufficient section modulus or moment of inertia in the direction of movement of second portion 42 to resist bending, bowing, and/or deflection forces applied during such movement.

In one specific embodiment, first portion 22 and second portion 42 are each made from surgical grade stainless steel. Other materials are also contemplated for first and second portions 22, 42, including, for example, plastics and metals and metal alloys, such as, for example, spring steel, shape memory metals and alloys, and aluminum.

Figure 2:
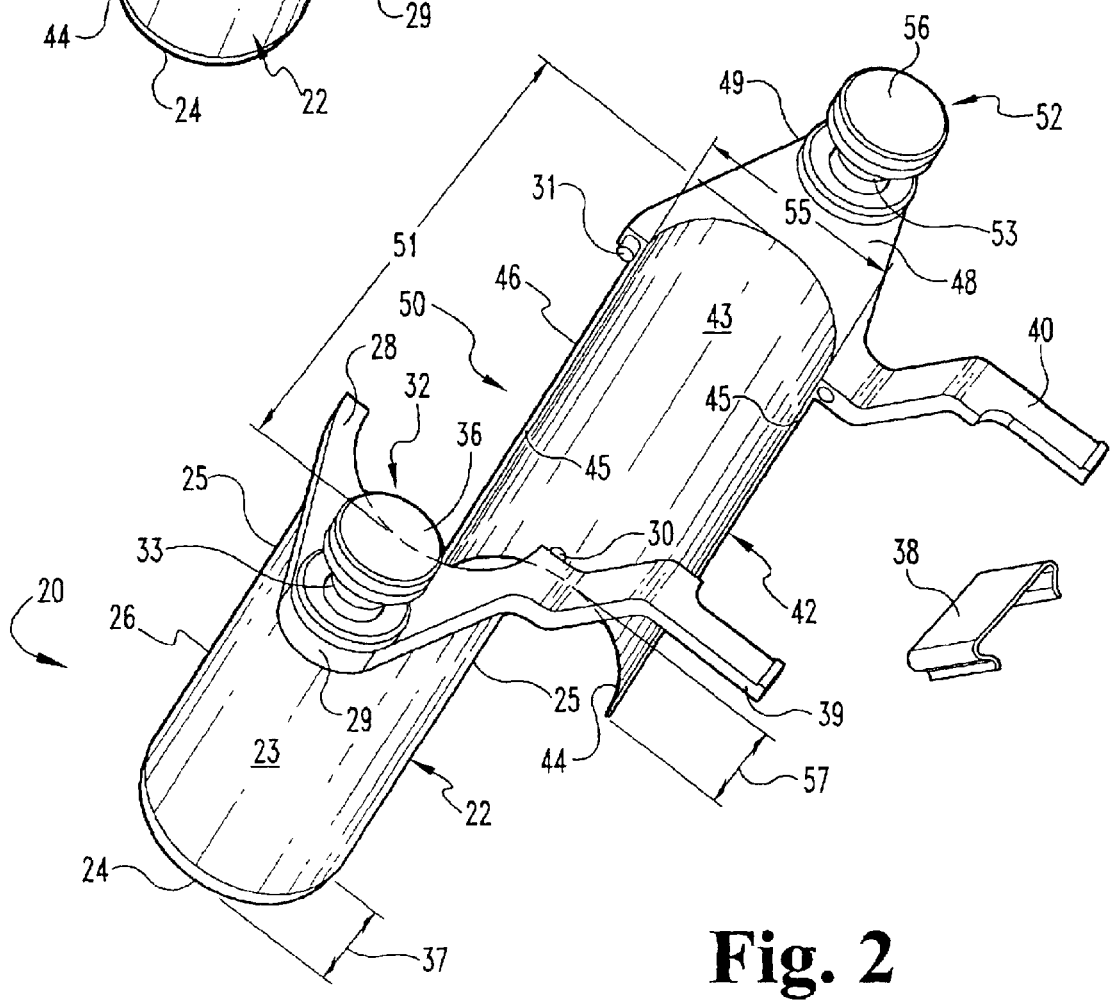
FIG. 2 is a perspective view of the retractor of FIG. 1 with first and second portions of the retractor separated from one another.
Figure 8:
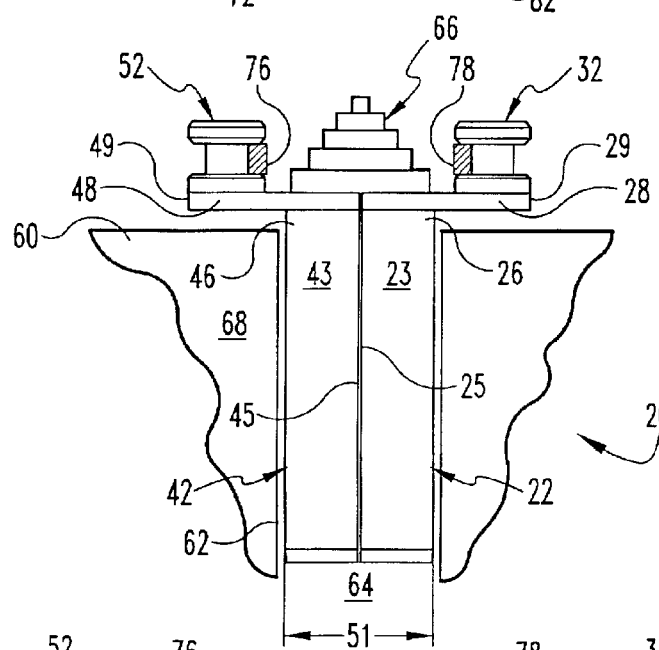
FIG. 8 is a section view through line 8—8 of FIG. 7 in which the retractor has been inserted over sequential tissue dilators.

In the initial insertion configuration, working channel 50 has a generally circular cross-section along retractor 20, as shown in FIGS. 1, 7 and 8. Working channel 50 has a first width 51 in the direction of movement of first portion 22 relative to second portion 42, and a second width 55 extending from one of the pair of adjacent edges 25, 45 to the other of the pair of adjacent edges 25, 45. In the illustrated embodiment, first and second widths 51 and 55 can be substantially the same since working channel 50 has a generally circular cross-section in its initial insertion configuration. In the enlarged configuration, as shown in FIGS. 2 and 9, second width 55 remains generally the same as in the initial insertion configuration for retractor 20, while first width 51 is increased by separating first portion 22 and second portion 42.

Various configurations for working channel 50 are contemplated. In the initial insertion configuration, working channel 50 can have a cylindrical shape with, for example, a circular, oval, elliptical, polygonal, or combined polygonal/curved cross-sectional shape. In the enlarged configuration, working channel 50 can have a cylindrical or frusto-conical shape with, for example a cross-section that is oval, elliptical, circular, curved, polygonal, or combined polygonal/curved in shape.

One specific application for retractor 20 is in spinal surgery. It is contemplated that, after insertion of retractor 20, first portion 22 and second portion 42 are separated predominantly in one direction to retract muscle and tissue along pathway 62 (FIG. 7.) For example, first and second portions 22, 42 of retractor 20 can be primarily or predominantly separable in the direction of the spinal column axis. The muscle tissue adjacent the spine has a fiber orientation that extends generally in the direction of the spinal column axis. The separation of body portions 23, 43 of retractor 20 separates the muscle tissue along the fibers, thus the amount of separation and the resultant tearing and trauma to the muscle tissue can be minimized. It is also contemplated in other techniques employing retractor 20 that working channel 50 can be enlarged primarily in a direction other than along the spinal column axis or in areas other than spine. Embodiments of retractor 20 are also contemplated in which working channel 50 is enlarged substantially in one direction or in all directions.

Figure 9:
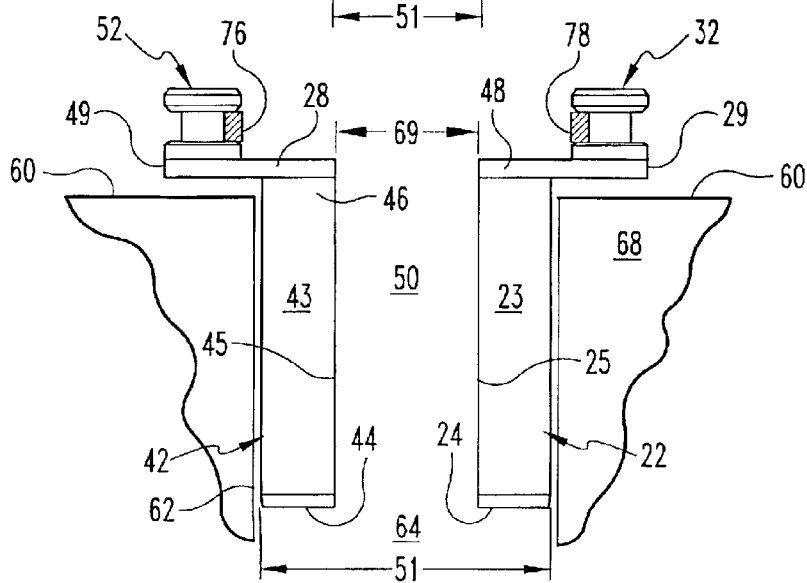
FIG. 9 is the retractor of FIG. 8 with the working channel of the retractor enlarged.

Referring now to FIGS. 7–9, one example of a method for positioning of retractor 20 through the skin 60 and tissue 68 of the patient will be described. An incision is made in skin 60 adjacent the location of a patient's anatomy to be accessed. For example, in spinal surgery, the incision can be made at a vertebral level at a location that provides access to the disc space between adjacent vertebrae or to one or more vertebra through a desired approach. Prior to insertion of retractor 20, skin 60 and tissue 68 can be sequentially dilated via dilation instrument set 66 which can include guidewires and/or one or more tissue dilators of increasing size. The tissue dilators are inserted one over another to form a pathway 62 through skin 60 and tissue 68 to the surgical site in the patient. In such procedures, retractor 20 is positioned over the last inserted dilator to form pathway 62 in the skin and tissue. Working channel 50 through retractor 20 provides access to a working space 64 at the distal end of retractor 20 when the guidewires and dilators, if used, are removed therefrom.

For the entire surgery or for certain procedures during the surgery, it may be desired by the surgeon to increase the size of working channel 50 to facilitate access working space 64 below the distal end of retractor 20, or to increase the size of working space 64. First and second portions 22, 42 of retractor 20 can be separated from their insertion configuration to a separated configuration in which working channel 50 is enlarged, as shown in FIG. 9. In the enlarged configuration, first portion 22 and second portion 42 can be moved laterally and/or pivoted away from one another by a separation instrument. One example of a separation instrument is separation instrument 70 extending between and coupled to engagement members 32, 52. Adjacent ones of the edges 25, 45 are separated by a space 69, exposing working channel 50 to the skin and tissue along pathway 62 while first and second portions 22, 42 hold tissue out of the operative field. In the enlarged configuration, working channel 50 and thus pathway 62 are enlarged through the through skin 60 and tissue 68 formed by first portion 22 and second portion 42. The size of working space 64 can be increased while minimizing trauma to the tissue and skin along pathway 62.

First and second portions 22, 42 can be pivoted or rotated away from one another about their proximal ends to provide working channel 50 with a tapered configuration that reduces in size from the distal end of retractor 20 adjacent working space 64 through skin 60 to the proximal end of retractor 20. A tapered working channel provides the surgeon greater access and increased visualization of working space 64 while minimizing tissue retraction. The tapered working channel 50 also allows greater angulation of instruments placed through working channel 50, more selection in positioning of instruments within working channel 50, and the ability to position instruments adjacent the inner wall surfaces of the separated first and second portions 22, 42, increasing the room available at working space 64 for multiple instruments.

Viewing instruments can be positioned in or adjacent to working channel 50 to facilitate surgeon viewing of working space 64 and the operative site. For example, an endoscopic viewing element can be mounted on the proximal end of retractor 20 with a scope portion extending along working channel 50. A microscopic viewing element can be positioned over the proximal end of retractor 20 for viewing working space 64 and the surgical site. Other imaging techniques, such as lateral fluoroscopy, can be used alone or in combination with the endoscopic and microscopic viewing elements. It is further contemplated that other instruments can be mounted on the proximal end of retractor 20, such as nerve root retractors, tissue retractors, forceps, cutter, drills, scrapers, reamers, separators, rongeurs, taps, cauterization instruments, irrigation and/or aspiration instruments, illumination instruments and the like for use in surgical procedures through retractor 20 in the working space. Such viewing instruments and other instruments can be employed with working channel 50 in its initial insertion configuration and/or its enlarged configuration.

Referring now to FIG. 7, further details regarding one embodiment instrument 70 for separating first and second portions 22, 42 will be provided. Instrument 70 includes a rack portion 72 and a body portion 74. Rack portion 72 includes a foot portion 76 releasably engageable to engagement member 52, and body portion 74 includes a foot portion 78 releasably engageable to engagement member 32. Rack portion 72 includes an extension 80 received through a housing 82 of body portion 74. Housing 82 includes a pinion 84 rotatably mounted therein and engaged with teeth 86 of extension 80. Pinion 84 can be engaged by a tool or manually by the surgeon and rotated to move rack portion 72 relative to body portion 74, thereby moving feet portion 76, 78 away from one another to separate first portion 22 and second portion 42 to enlarge working channel 50. A stop member 88 can be provided at the end of or at any position along extension 80 to prevent over-separation of first portion 22 and second portion 42.

Figure 10:
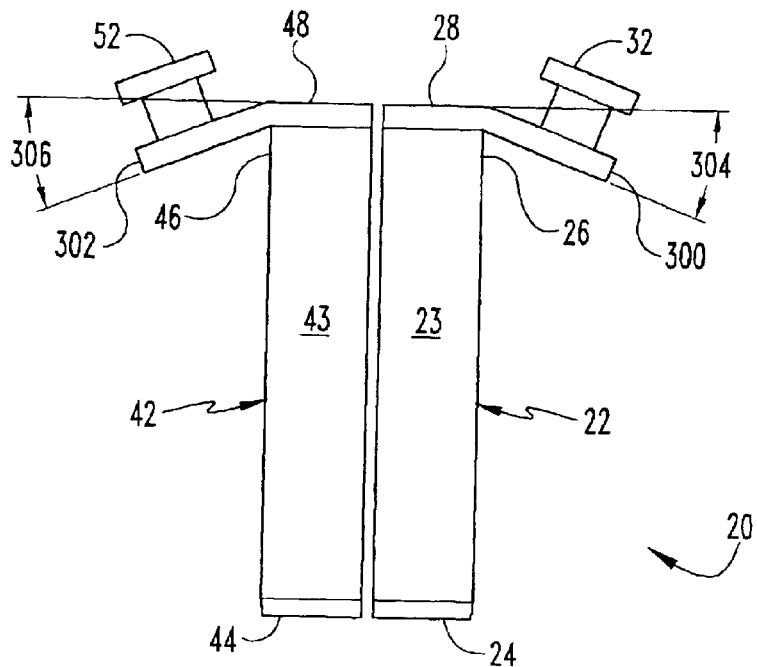
FIG. 10 is a side view of another embodiment retractor in an insertion configuration.
Figure 11:
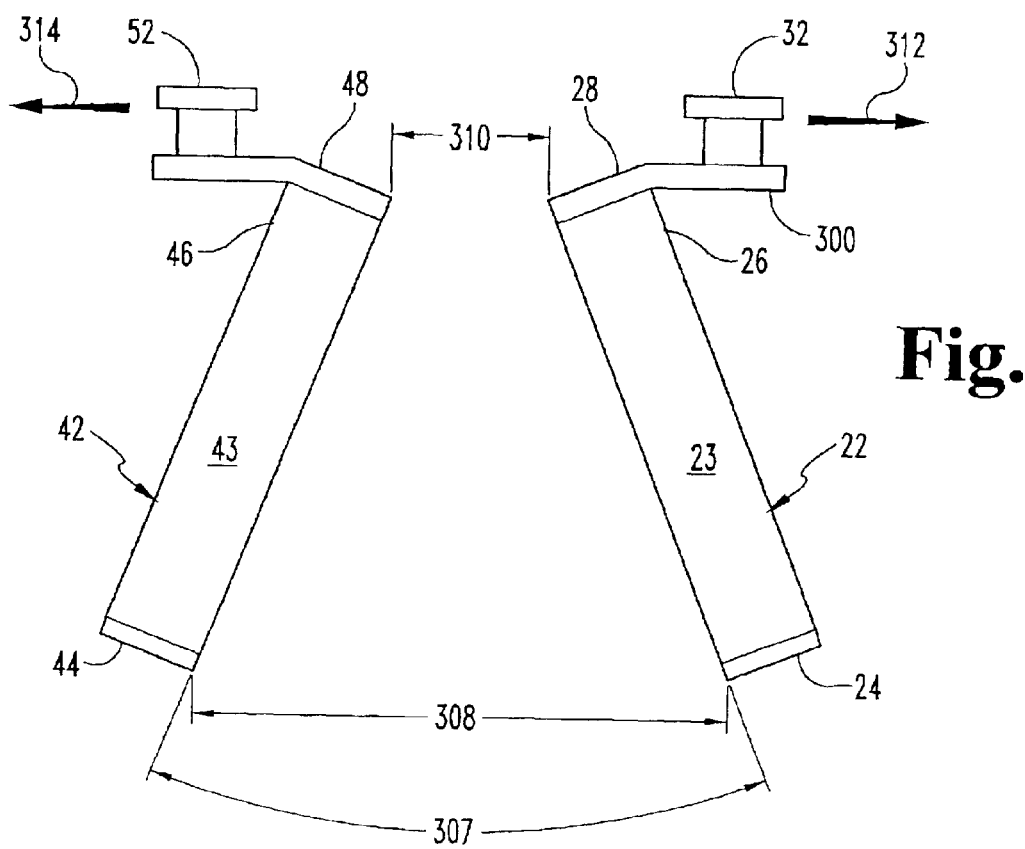
FIG. 11 is the retractor of FIG. 10 with the working channel enlarged.

Referring now to FIGS. 10 and 11, another embodiment retractor 20 is shown in which retractor portions 22, 42 are simultaneously separable from one another and pivotal relative to one another to enlarge working channel 50. Collar 28 includes an extension 300 extending from body 23 of first portion 22 generally in the direction of separation of first portion 22 from second portion 42. Collar 48 includes an extension 302 extending from body 43 of second portion 42 generally in the direction of separation of second portion 42 from first portion 22. In the insertion configuration of FIG. 10, extension 300 extends distally from collar 28 at an angle 304, and extension 302 extends distally from collar 48 at an angle 306. Engagement members 32, 52 extend proximally from respective ones of the extensions 300, 302.

In FIG. 11, working channel 50 has been enlarged by application of a lateral separation force with, for example, separation instrument 70 discussed above or instrument 220 discussed below, as indicated by arrows 312, 314. The lateral separation forces move first portion 22 away from second portion 42. The lateral separation forces are applied to the engagement members 32, 52 on the angled extensions 300, 302. Angled extensions 300, 302 tend to cause distal ends 24, 44 to pivot or rotate away from one another as angled extensions 300, 302 are rotated or pivoted in the direction in which lateral forces 314, 316 are applied. As a result, edges 25, 45 form angle 307 therebetween and provide working channel 50 with an enlarged, frusto-elliptical shape between the distal ends 24, 44 and proximal ends 26, 46. Distal ends 24, 44 are separated at edges 25, 45 by a distance 308, which is greater than the distance 310 separating edges 25, 45 adjacent proximal ends 26, 46.

Figure 12:
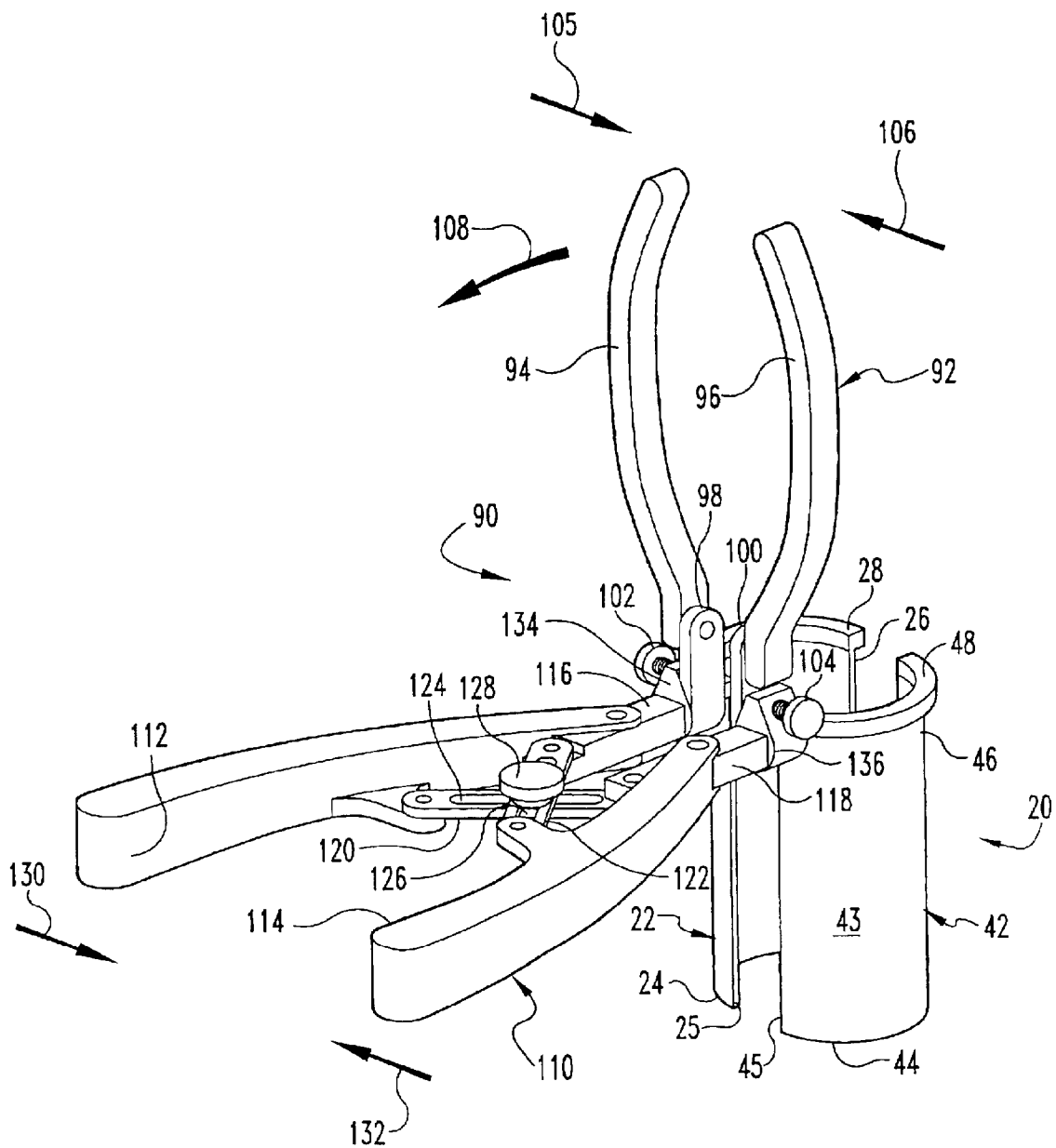
FIG. 12 is a perspective view of another embodiment retractor and instrument for separating first and second portions of the retractor.

Referring now to FIG. 12, there is shown retractor 20 with another embodiment instrument 90 for separating first portion 22 and second portion 42. Instrument 90 includes a rotational separator 92 and a lateral separator 110. Rotational separator 92 is operable to rotate or pivot first portion 22 and second portion 42 relative to one another about their proximal ends 26, 46 to move distal ends 24, 44 away from one another. Lateral separator 110 is operable to move first portion 22 and second portion 24 away from one another by separating proximal ends 26, 46 and distal ends 24, 44 laterally. As discussed further below, instrument 90 can be coupled to engagement members (not shown) of the first and second portions 22, 42 located adjacent one of the edges 25, 45 and extending laterally from the respective first and second portions 22, 42. Rotational separator 92 and lateral separator 110 can be operated sequentially to pivot then laterally separate, or laterally separate and then pivot first and second portions 22, 42. Rotational separator 92 and lateral separator 110 can also be operated simultaneously to pivot/rotate and laterally separate first and second portions 22, 42.

Rotational separator 92 includes a first handle 94 and a second handle 96. First handle 94 is mounted to a first coupling member 98, and second handle 96 is mounted to a second coupling member 100. First coupling member 98 of rotational separator 92 is non-rotatably coupled to the lateral engagement member of first portion 22, and second coupling member 100 of rotational separator 92 is non-rotatably coupled to the lateral engagement member of second portion 42. First and second portions 22, 42 are pivotal or rotatable away from one another by moving first handle 94 in the direction of arrow 105 toward second handle 96, and by moving second handle 96 in the direction of arrow 106 toward first handle 94. Movement of handles 94, 96 in the direction of arrows 105, 106 rotates the proximal ends of coupling members 98, 100 toward one another to effect the pivotal or rotational movement of first and second portions 22, 42. Handles 94, 96 can be pivotally coupled to connectors 98, 100 for rotation in the direction of arrow 108 to move handles 94, 96 away from the proximal end opening of working channel 50 and provide the surgeon clear access thereto.

Lateral separator 110 extends laterally from retractor 20 transversely to the direction of separation of first portion 22 and second portion 42. Lateral separator 110 includes a first handle 112 and a second handle 114. A first coupling member 116 is pivotally coupled at a mid-portion thereof to first handle 112, and a second coupling member 118 is pivotally coupled at a mid-portion thereof to second handle 114. Coupling members 116, 118 are rotationally coupled at their distal ends to respective ones of the lateral engagement members extending from first portion 22 and second portion 42. A first link 120 extends between and is pivotally coupled at one end to first handle 112 and at its opposite end to second coupling member 118. A second link 122 extends between and is pivotally coupled at one end to second handle 114 and at its opposite end to first coupling member 116. First coupling member 116 includes a first tab 134 that rotatably receives the lateral engagement member extending from first portion 22. Second coupling member 118 includes a second tab 136 that rotatably receives the lateral engagement member extending from second portion 42.

First link 120 includes a first slot 124, and second link 122 includes a second slot 126. A locking pin 128 extends through slots 124, 126 and couples links 120, 122 to one another. To laterally separate first portion 22 from second portion 42, locking pin 128 is loosened so the links 120, 122 are movable relative to one another. First handle 112 is moved in the direction of arrow 130 toward second handle 114, and second handle 114 is moved in the direction of arrow 132 toward first handle 112. First link 120 pushes outwardly on second coupling member 118 while second handle 114 pulls outwardly on second coupling member 118. Similarly, second link 122 pushes outwardly on first coupling member 116 while first handle 112 pulls outwardly on first coupling member 116. Coupling members 116, 118 thus laterally move away from one another. This separates first and second portions 22, 42 such that edges 25, 45 are displaced laterally the same relative distance from one another between proximal ends 26, 46 and distal ends 24, 44. Locking pin 128 can then be threaded to clamp link members 120, 122 together and prevent further movement of lateral separator 110. Movement of handles 112, 114 in the direction opposite arrows 130, 132 moves first and second portion 22, 42 toward one another, and, if pivoted, movement of handles 94, 96 toward one another can pivot first and second portions 22, 42 toward one another to reduce working channel 50 for easier removal of retractor 20 from the incision.

First and second adjustment mechanisms 102, 104 are provided for small incremental adjustment in the rotational positioning of first portion 22 and second portion 42, respectively. First adjustment mechanism 102 extends through first tab 134 and engages first coupling member 98. As first adjustment mechanism 102 is threaded toward first tab 134, the end of first adjustment mechanism 102 pushes on first coupling member 98, causing first coupling member 98 and first handle 94 along with first portion 22 to pivot or rotate relative first tab 134. Adjustment mechanism 102 can also engage first coupling member 98 to maintain first portion 22 in a pivoted or rotated position provided through first handle 94. Similarly, second adjustment mechanism 104 extends through second tab 136 and engages second coupling member 100. As second adjustment mechanism 104 is threaded toward second tab 136, the end of second adjustment mechanism 104 pushes on second coupling member 100, causing second coupling member 100 and second handle 96 along with second portion 42 to pivot or rotate relative second tab 136. Second adjustment mechanism 104 can also engage second coupling member 100 and maintain second portion 42 in a pivoted or rotated position provided through second handle 96.

In use, the resistance to retraction provided by the tissue may prevent distal ends 24, 44 from separating as far as proximal ends 26, 46 when a separation force is applied with lateral separator 110. Rotational separator 92 can be used to move distal ends 24, 44 away from one another to provide the desired separation between edges 25, 45 along the length of first and second portions 22, 42.

Figure 13:
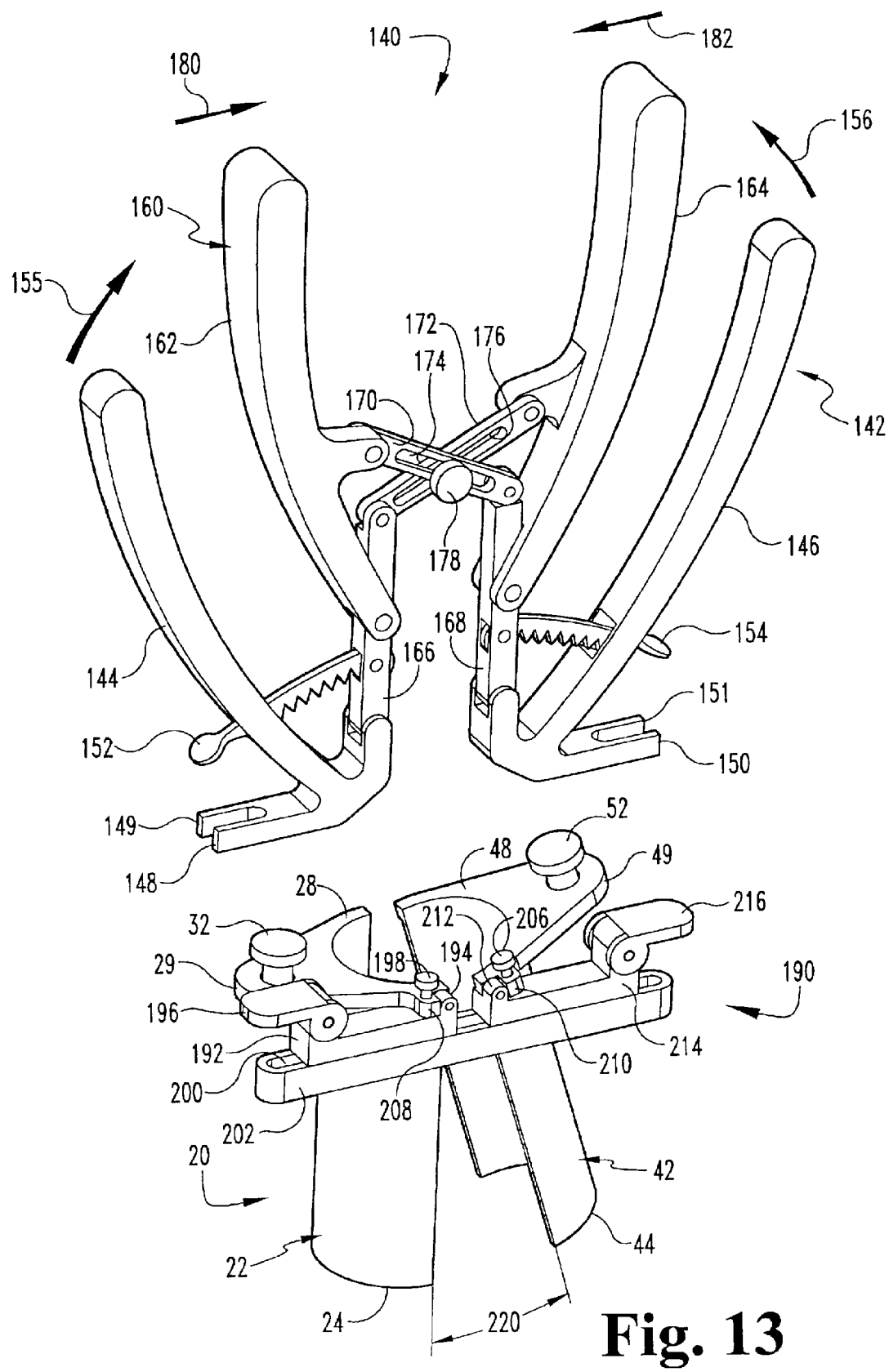
FIG. 13 is a perspective view of another embodiment retractor and instrument for separating first and second portions of the retractor.

Referring now to FIG. 13, there is shown retractor 20 with another embodiment instrument 140 for separating first portion 22 and second portion 42. Instrument 140 includes a rotational separator 142 and a lateral separator 160. Rotational separator 142 is operable to rotate or pivot first portion 22 and second portion 42 relative to one another about their proximal ends 26, 46 to move distal ends 24, 44 away from one another. Lateral separator 160 is operable to move first portion 22 and second portion 24 away from one another by separating proximal ends 26, 46 and distal ends 24, 44 laterally. Rotational separator 142 and lateral separator 160 can be operated sequentially to pivot then laterally separate, or laterally separate and then pivot first and second portions 22, 42. Rotational separator 142 and lateral separator 160 can also be operated simultaneously to pivot/rotate and laterally separate first and second portions 22, 42.

Rotational separator 142 includes a first handle 144 and a second handle 146. First handle 144 has a first coupling member 148, and second handle 146 has a second coupling member 150. First coupling member 148 includes a slot 149 to receive engagement member 32 of first portion 22, and second coupling member 150 includes a slot 151 to receive engagement member 52 of second portion 42. First and second portions 22, 42 are pivotal or rotatable away from one another by moving first handle 144 in the direction of arrow 155 toward second handle 146, and by moving second handle 146 in the direction of arrow 156 toward first handle 144. Movement of handles 144, 146 in the direction of arrows 155, 156 moves coupling members 148, 150 away from one another to effect the pivotal or rotational movement of first and second portions 22, 42 relative to one another.

Lateral separator 160 includes a first handle 162 and a second handle 164. A first connector 166 is pivotally coupled at a mid-portion thereof to first handle 162, and a second connector 168 is pivotally coupled at a mid-portion thereof to second handle 164. Connectors 166, 168 are pivotally coupled at their distal ends to respective ones of first handle 144 and second handle 146 of rotational separator 142.

A first link 170 extends between and is pivotally coupled at one end to first handle 162 and at its opposite end to second connector 168. A second link 172 extends between and is pivotally coupled at one end to second handle 164 and at its opposite end to first connector 166. First connector 166 includes a first locking member 152 pivotally coupled thereto that can extend through and releasably engage first handle 144. Second connector 168 includes a second locking member 154 pivotally coupled thereto that can extend through and releasably engage second handle 146. Locking members 152, 154 can selectively engage and maintain the positioning of handles 142, 144 at any one of a number of positions to which first portion 22 and second portion 42 have been rotated or pivoted by rotational separator 142.

First link 170 includes a first slot 174, and second link 172 includes a second slot 176. A locking pin 178 extends through slots 174, 176 and couples links 170, 172 to one another. To laterally separate first portion 22 from second portion 42, locking pin 178 is loosened so links 170, 172 are movable relative to one another. First handle 162 is moved in the direction of arrow 180 toward second handle 164, and second handle 164 is moved in the direction of arrow 182 toward first handle 162. First link 170 pushes outwardly on second coupling member 168 while second handle 164 pulls outwardly on second coupling member 168. Similarly, second link 172 pushes outwardly on first coupling member 166 while first handle 162 pulls outwardly on first coupling member 166. Coupling members 166, 168 laterally move connecting portions 148 away from one another. Thus, actuation of handles 162, 164 laterally separates the connected first and second portions 22, 42 such that edges 25, 45 are laterally displaced relative to one another between proximal ends 26, 46 and distal ends 24, 44. Locking pin 178 can then be threaded to clamp link members 170, 172 together and prevent further movement of lateral separator 160. Movement of handles 162, 164 in the direction opposite arrows 180, 182 moves first and second portion 22, 42 toward one another to reduce the spacing therebetween for easier removal of retractor 20 from the incision.

In use, the resistance to retraction provided by the tissue may prevent distal ends 24, 44 from separating as far as proximal ends 26, 46 when a separation force is applied with lateral separator 160. Rotational separator 142 can be used to move distal ends 24, 44 away from one another to provide the desired separation between edges 25, 45 along the length of first and second portions 22, 42.

Instrument 140 is positioned over the proximal end opening of working channel 50. To provide clear access to working channel 50 for the surgeon, instrument 140 can be removed from retractor 20, and a guide mechanism 190 can maintain the lateral and rotational positioning of first portion 22 and second portion 42 obtained with instrument 140. Guide mechanism 190 includes a guide member 200 having a slot 202 formed therein. Guide member 200 extends between first portion 22 and second portion 42 along one side thereof, and first and second portions 22, 42 are coupled thereto. It is also contemplated that a second guide member could be provided on the other side of retractor 20.

A first coupling member 192 is movably mounted in slot 202 of guide member 200 adjacent first portion 22, and a second coupling member 214 is movably mounted in slot 202 of guide member 200 adjacent second portion 42. First portion 22 includes a first ear 208 extending from collar 28 pivotally coupled at one end 194 of first coupling member 192. At the other end of first coupling member 192 is a cam locking mechanism 196 that is releasably engageable to guide member 200 to maintain the positioning of first portion 22 along guide member 200. Second portion 42 includes a second ear 210 extending from collar 48 that is pivotally coupled at one end 212 of second coupling member 214. At the other end of second coupling member 214 is a cam locking mechanism 216 that is releasably engageable to guide member 200 to maintain the positioning of second portion 42 along guide member 200.

First and second adjustment mechanisms 198, 206 are provided for small incremental adjustment in the rotational positioning of first portion 22 and second portion 42, respectively. First adjustment mechanism 198 extends through first ear 208 and engages first coupling member 192. As first adjustment mechanism 198 is threaded toward first ear 208, the end of first adjustment mechanism 198 engages first coupling member 192, maintaining first portion 22 in its pivoted position relative to guide member 200. First adjustment mechanism 198 can also be manipulated by the surgeon for small adjustments in the pivotal position of first portion 22 relative to guide member 200 and second portion 42. Second adjustment mechanism 206 extends through second ear 210 and engages second coupling member 214. As second adjustment mechanism 206 is threaded toward second ear 210, the end of second adjustment mechanism 206 engages second coupling member 214 to maintain second portion 42 in its pivoted position relative to guide member 200. Second adjustment mechanism 206 can also be manipulated by the surgeon to make adjustments in the pivotal position of second portion 42 relative to guide member 200 and first portion 22.

Figure 14:
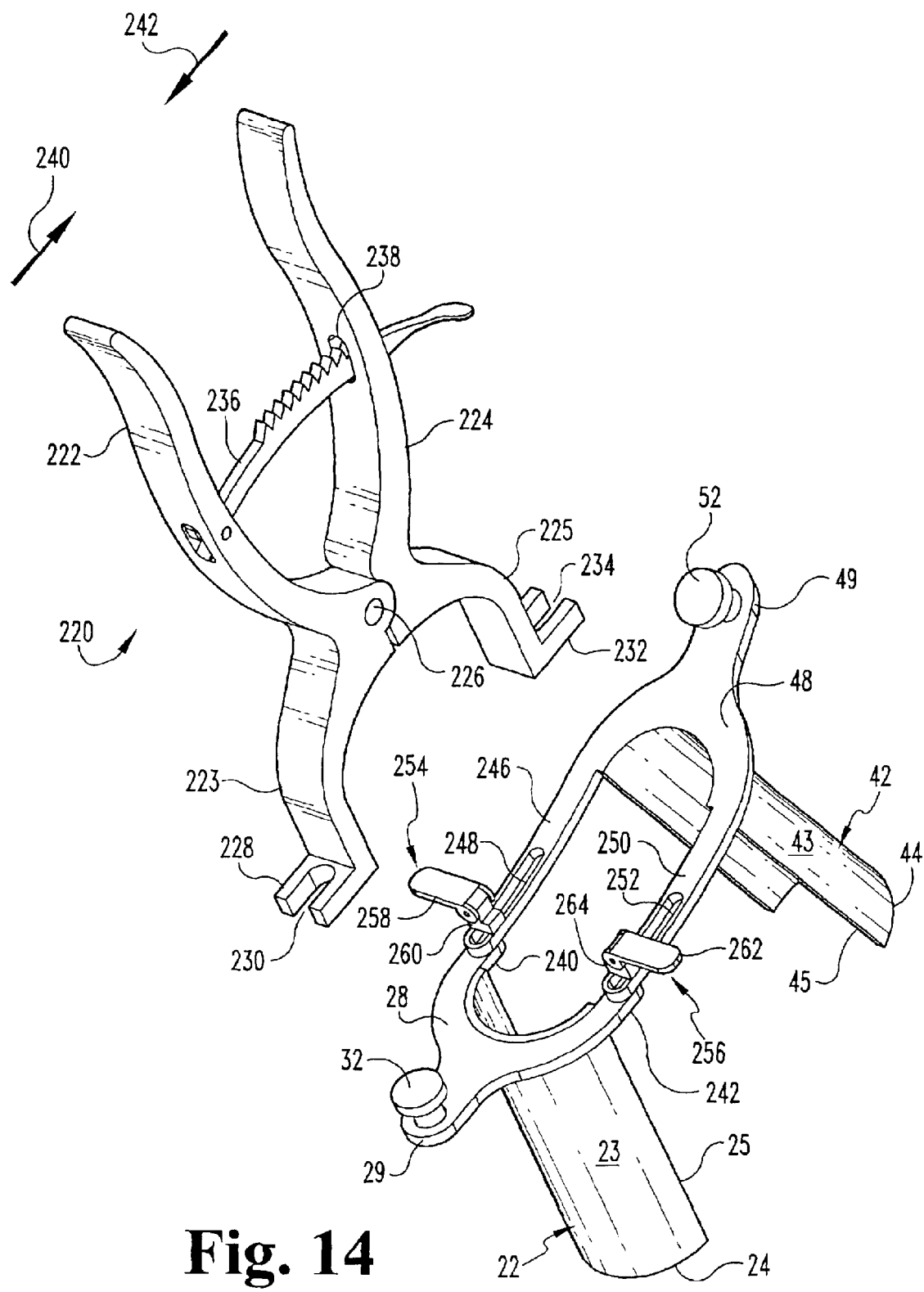
FIG. 14 is a perspective view of another embodiment retractor and instrument for separating first and second portions of the retractor.

Referring now to FIG. 14, there is shown another embodiment instrument 220 for separating first and second portions 22, 42 of retractor 20. Instrument 220 includes a first handle 222 pivotally coupled to a second handle 224 about pin 226. First handle 222 includes a distal portion 223 having a coupling member 228. Coupling member 228 includes a slot 230 for receiving engagement member 32 of first portion 22 therein. Second handle 224 includes a distal portion 225 having a coupling member 232. Coupling member 232 includes a slot 234 for receiving engagement member 52 of second portion 42 therein. A locking member 236 is pivotally coupled at one end to first handle 222, and extends through slot 238 of second handle 224 for releasable locking engagement therewith.

In use, instrument 220 is mounted on retractor 20 with coupling members 228, 232 in engagement with respective ones of engagement members 32, 52. Handles 222, 224 are moved toward one another in the direction indicated by arrows 240, 242 to move coupling members 228, 232 away from one another. In turn, first portion 22 and second portion 42 are separated from one another.

Retractor 20 can be adapted to guide first and second portions 22, 42 during separation and to maintain the separation provided with instrument 220. In the illustrated embodiment, collar 28 of first portion 22 includes opposite first and second ears 240, 242 extending beyond the adjacent edges 25 toward second portion 42. Second portion 42 includes first guide member 246 positionable over first ear 240, and second guide member 250 positionable over second ear 242. First guide member 246 includes a slot 248 and second guide member 250 includes a slot 252. A first cam locking mechanism 254 extends through slot 248 and couples first ear 240 to first guide member 248. A second cam locking mechanism 256 extends through slot 252 and couples second ear 242 to second guide member 250.

First cam locking mechanism 254 includes a lever 258 that clamps a locking body 260 against first ear 240 and first guide member 246, as shown in FIG. 14. Similarly, second cam locking mechanism 256 includes a lever 262 that clamps a locking body 264 against second ear 242 and second guide member 250, as shown in FIG. 14. When it is desired to move first portion 22 and/or second portion 42, levers 258 and 262 are rotated to release the respective clamped locking body 260, 264, respectively. Instrument 220 can then be used to apply a separation force, or first and second portions 22, 42 can be moved toward one another for easy removal from the incision.

It is contemplated that guide members 246, 250 can be curved or arcuate to follow the path of coupling members 228, 232 as coupling members 228, 232 are separated with handles 222, 224. In this manner, first portion 22 and second portion 42 are simultaneously pivoted/rotated and laterally separated with instrument 220. It is further contemplated that one or more guide members between first portion 22 and second portion 42 could be configured to provide only a lateral separation path or only a rotational separation path. Other embodiments contemplate guide members which provide a combined rotational and lateral separation path.

It is contemplated that for spinal surgery various retractors 20 can be provided in a kit with lengths ranging from 20 millimeters to 100 millimeters in increments of 10 or 20 millimeters. It is further contemplated that retractor 20 can be provided in a kit with various sized working insertion configurations, such as 14, 16, 18, 20, 21 or 25 millimeters for initial insertion width 55. It should be understood, however, that the present invention contemplates that retractor 20 can have other lengths and diameters and can be provided in a kit with different increments. The appropriate length for retractor 20 will depend on the depth of the desired surgical location below the skin of the patient, the anatomical location of the surgery, and the patient's anatomy. These factors in retractor selection can be evaluated through pre-operative planning prior to surgery by x-rays or other known imaging technique, and can be adjusted during the surgical procedure if necessary since retractors of differing lengths and working channel sizes can be made available.

While the invention has been illustrated and described in detail in the drawings and foregoing description, the same is to be considered as illustrative and not restrictive in character, and that all changes and modifications that come within the spirit of the invention are desired to be protected.

What is claimed is:

1. A tissue retractor for percutaneous surgery in a patient, comprising:
    a first portion having a proximal end and a distal end; and
    a second portion having a proximal end and a distal end, said second portion forming with said first portion a working channel in communication with an exterior of said first and second portions at said proximal ends and said distal ends with said working channel being enclosed by said first portion and said second portion between said distal and proximal ends, wherein said working channel is enlargeable by laterally moving each of said first and second portions away from one another and pivoting each of said distal ends of said first and second portions away from one another such that only a portion of said working channel is enclosed by said first and second portions.

2. The retractor of claim 1, further comprising a first bracket member extending from said proximal end of said first portion and a second bracket member extending from said proximal end of said second portion, wherein said first and second bracket members are positionable adjacent one another for engagement with a flexible arm.

3. The retractor of claim 1, wherein said first portion includes a collar about said proximal end thereof and said second portion includes a collar about said proximal end thereof, each of said collars including an engagement member extending proximally therefrom.

4. The retractor of claim 1, wherein each of said first and second portions includes a semi-cylindrical body.

5. The retractor of claim 4, wherein said bodies of said first and second portions are rigid.

6. The retractor of claim 1, wherein:
    said first portion includes opposite edges extending therealong between said proximal end and said distal end thereof;
    said second portion includes opposite edges extending therealong between said proximal end and said distal end thereof;
    when said working channel is enclosed said opposite edges of said first portion are adjacent respective ones of said opposite edges of said second portion; and
    when said working channel is enlarged said opposite edges of said first portion are separated from respective ones of said opposite edges of said second portion.

7. The retractor of claim 6, wherein said opposite edges of said first portion abut with an adjacent one of said opposite edges of said second portion when said working channel is substantially enclosed by said first and second portions.

8. The retractor of claim 6, wherein said opposite edges of said first portion overlap with an adjacent one of said opposite edges of said second portion when said working channel is substantially enclosed by said first and second portions.

9. The retractor of claim 6, wherein said opposite edges of said first portion interdigitate with an adjacent one of said opposite edges of said second portion when said working channel is substantially enclosed by said first and second portions.

10. The retractor of claim 1, wherein:
    one of said first portion and said second portion includes an alignment member extending toward the other of said first portion and said second portion; and
    the other of said first portion and said second portion includes a receptacle for receiving said alignment member.

11. The retractor of claim 10, wherein said alignment member extends from an edge of said one of said first portion and said second portion facing the other of said first portion and said second portion, and said receptacle is formed in an edge of said other of said first portion and said second portion facing said one of said first portion and said second portion.

12. The retractor of claim 1, further comprising a guide member extending between said first portion and said second portion, each of said first portion and said second portion engageable with said guide member to secure said first portion and said second portion at any one of a number of locations along said guide member.

13. The retractor of claim 12, wherein each of said first and second portions are further engageable with said guide member to secure said first and second portions at any one of a number of pivotal orientations relative to said guide member.

14. The retractor of claim 12, further comprising a separation instrument engageable to said proximal ends of said first and second portions, said separation instrument operable to move at least one of said first and second portions along said guide member.

15. The retractor of claim 14, wherein said guide member includes an arcuate profile between said first portion and said second portion and said separation instrument is operable to simultaneously separate and pivot said first and second portions away from one another along said guide member.

16. The retractor of claim 14, wherein said separation instrument has a lateral separator operable to laterally separate said first and second portions along said guide member and a rotational separator operable to pivot said first and second portions relative to said guide member.

17. The retractor of claim 12, wherein said guide member is pivotally coupled to said proximal ends of each of said first and second portions.

18. The retractor of claim 12, wherein:
said first portion includes an ear extending from said proximal end thereof toward said second portion;
said guide member is an extension of said proximal end of said second portion; and
said ear is engageable with said guide member.

19. The retractor of claim 18, wherein said guide member includes a slot, and further comprising a cam locking mechanism extending through said slot and coupled to said ear, said cam locking mechanism having a first position locking said ear to said guide member and a second position wherein said ear is moveable along said guide member.

20. The retractor of claim 1, further comprising a separation instrument engageable to said first and second portions, said separation instrument including a lateral separator for laterally separating said first and second portions and a rotational separator for pivoting said first and second portions relative to one another.

21. The retractor of claim 20, wherein:
said lateral separator extends laterally from said first and second portions transversely to a lateral separation direction of said first and second portions; and
said rotational separator extends proximally from said first and second portions.

22. The retractor of claim 21, wherein said rotational separator is pivotal to a lateral orientation along said lateral separator to clear access to said working channel from said proximal ends of said first and second portions.

23. The retractor of claim 1, wherein said working channel has a generally circular cross-section when enclosed by said first and second portions and a generally oval cross-section when said first and second portions are separated.

24. A tissue retractor for percutaneous surgery in a patient, comprising:
a first portion and a second portion adjacent said first portion, said first and second portions each having a length between a distal end and a proximal end thereof such that said proximal ends are positionable outside the patient and said distal ends are positionable in the patient;
a working channel between said first and second portions sized to receive at least one surgical instrument for performance of a surgical procedure; and
said working channel having an insertion configuration wherein said working channel has a cross-section circumscribed by said first and second portions and an enlarged configuration wherein each of said first and said portions are laterally separable and pivotable relative to one another to provide said working channel with a cross-section circumscribeable by each of said first and second portions and tissue of the patient between said first and second portions when said working channel is enlarged in the patient.

25. The retractor of claim 24, wherein said cross-section of said working channel is circular in said insertion configuration and said cross-section of said working channel is oval in said enlarged configuration.

26. The retractor of claim 24, wherein said first portion includes opposite edges extending between said distal and proximal ends thereof, said second portion includes opposite edges extending between said distal and proximal ends thereof abutting said edges of said first portion with said working channel in said insertion configuration.

27. The retractor of claim 24, wherein:
said first portion includes opposite edges extending therealong between said proximal end and said distal end thereof;
said second portion includes opposite edges extending therealong between said proximal end and said distal end thereof;
when said working channel is in said insertion configuration said opposite edges of said first portion are adjacent respective ones of said opposite edges of said second portion; and
when said working channel is in said enlarged configuration said opposite edges of said first portion are separated from respective ones of said opposite edges of said second portion.

28. The retractor of claim 24, wherein each of said first and second portions has a body with a semi-circular cross-section.

29. The retractor of claim 24, wherein:
said first portion includes a first collar adjacent said proximal end having a first engagement member extending therefrom; and
said second portion includes a second collar adjacent said proximal end having a second engagement member extending therefrom.

30. The retractor of claim 29, wherein said first collar includes a first extension extending at a distal angle relative to said first collar and said second collar includes a second extension extending at a distal angle relative to said second collar, said first engagement member extending from said first extension and said second engagement member extending from said second extension.

31. The retractor of claim 29, wherein:
said first collar includes an ear extending therefrom toward said second portion;
said second collar includes a guide member extending therefrom toward said first portion; and
said ear is engageable at any one of a number of locations along said guide member as said first portion and said second portion are separated from one another.

32. The retractor of claim 31, further comprising a cain locking mechanism for releasably engaging said ear to said guide member.

33. The retractor of claim 29, further comprising a separation instrument removably engageable to said first and second engagement members.

34. The retractor of claim 33, wherein said separation instrument is configured for application of a lateral separation force and a pivotal separation force to said first and second portions.

35. The retractor of claim 24, further comprising a separation instrument removably engageable to each of said first and second portions.

36. The retractor of claim 35, wherein said separation instrument is operable to simultaneously laterally separate and pivotally separate said first and second portions.

37. A tissue retractor for percutaneous surgery in a patient, comprising:
a first portion extending between a proximal end and a distal end;
a second portion extending between a proximal end and a distal end, said first and second portions forming a working channel between said distal ends and said proximal ends of said first and second portions, said working channel having an insertion configuration wherein said working channel is substantially circumscribed by said first and second portions, said working channel further having an enlarged configuration wherein said first portion is separated from said second portion; and means for simultaneously laterally separating and pivoting each of said first and second portions relative to the other of said first and second portions.

38. The retractor of claim 37, wherein said means includes:
a first distally angled extension extending from said proximal end of said first portion and a first engagement member extending proximally from said first extension; and
a second distally angled extension extending from said proximal end of said second portion and a second engagement member extending proximally from said second extension.

39. The retractor of claim 37, wherein said means comprises a guide member extending between said first portion and said second portion, at least one of said first portion and said second portion being engageable with said guide member to secure said at least one of said first portion and said second portion at any one of a number of locations along said guide member.

40. The retractor of claim 39, wherein each of said first and second portions are movable along and pivotal with respect to said guide member.

41. The retractor of claim 39, wherein said means further comprises a separation instrument engageable to said proximal ends of said first and second portions, said separation instrument operable to move said at least one of said first and second portions along said guide member.

42. The retractor of claim 41, wherein said guide member includes an arcuate profile between said first portion and said second portion.

43. The retractor of claim 41, wherein said separation instrument has a lateral separator operable to laterally separate said first and second portions along said guide member and a rotational separator operable to pivot said first and second portions relative to said guide member.

44. The retractor of claim 39, wherein said guide member is pivotally coupled to a proximal end of said first portion and to a proximal end of said second portion.

45. The retractor of claim 39, wherein:
said first portion includes an ear extending from said proximal end thereof;
said guide member is an extension of said proximal end of said second portion;
and said ear is movably engaged with said guide member.

46. The retractor of claim 45, further comprising a second guide member extending between said first portion and said second portion opposite said guide member.

47. The retractor of claim 37, wherein said means comprises a separation instrument engageable to said first and second portions, said separation instrument including a lateral separator for laterally separating said first and second portions and a rotational separator for pivoting said first and second portions relative to one another.

48. The retractor of claim 37, wherein said means comprises a separation instrument engageable to said first and second portions, said separation instrument including:
a lateral separator extending laterally from said first and second portions transversely to a lateral separation direction of said first and second portions; and
a rotational separator for pivoting said first and second portions relative to one another, said rotational separator extending proximally from said first and second portions.

49. A kit for use in percutaneous surgery, comprising:
a retractor having a first portion and a second portion forming a working channel, said working channel having an insertion configuration wherein said working channel is substantially circumscribed by said first and second portions, said first and second portions separable from one another to open said working channel to an exterior of said retractor thereby enlarging said working channel;
at least one guide member extending between and coupling said first portion and said second portion to one another; and
a separation instrument engageable with said first and second portions and operable to separate and pivot each of said first and second portions relative to said guide member and to the other of said first and second portions.

50. The kit of claim 49, wherein each of said first and said second portions are engageable with said guide member to secure said first portion and said second portion at any one of a number of locations along said guide member.

51. The kit of claim 50, wherein each of said first and second portions are engageable with said guide member to secure said first and second portions any one of a number of pivotal orientations relative to said guide member.

52. The kit of claim 49, wherein said separation instrument is engageable to said proximal ends of said first and second portions, said separation instrument operable to laterally separate said first and second portion portions along said guide member.

53. The kit of claim 52, wherein said guide member includes an arcuate profile between said first and second portions.

54. The kit of claim 49, wherein said separation instrument has a lateral separator operable to laterally separate said first and second portions along said guide member and a rotational separator operable to pivot said first and second portions relative to said guide member.

55. The kit of claim 49, further comprising a set of sequential tissue dilators.

56. A kit for use in percutaneous surgery, comprising:
a retractor having a working channel extending between a proximal end and a distal end of said retractor, said retractor having a first portion and a second portion substantially circumscribing said working channel in an insertion configuration, said first and second portions separable from one another to enlarge said working channel; and
a separation instrument engageable to said first and second portions, said separation instrument having a lateral separator operable to laterally separate each of said first portion and said second portion from the other of said first portion and said second portion and a rotational separator operable to pivot each of said first portion and second portion relative to the other of said first portion and said second portion.

57. The kit of claim 56, wherein said lateral separator extends laterally from said first and second portions transversely to a lateral separation direction of said first and second portions and said rotational separator extends proximally from said first and second portions.

58. The kit of claim 57, wherein said rotational separator is pivotal to a lateral orientation along said lateral separator to clear access to said working channel from said proximal end of said retractor.

59. The kit of claim 56, wherein each of said lateral separator and said rotational separator extends proximally from said first and second portions.

60. The kit of claim 56, further comprising a dilator set comprising one or more tissue dilators.

61. The kit of claim 56, further comprising a view instrument for visualizing a surgical location in a patient.

62. The kit of claim 56, further comprising one or more surgical instruments insertable through the working channel.

63. A method for performing a surgical procedure at a location in a patient, comprising:

making an incision in skin and tissue of the patient to access the location;

forming a substantially enclosed working channel through the incision to the location by inserting a distal end of a retractor into the patient with a proximal end of the retractor located outside of the patient; and enlarging the working channel by laterally separating and pivoting each one of first and second portions of the retractor relative to the other of the first and second portions of the retractor to expose the working channel to tissue along the retractor.

64. The method of claim 63, further comprising:

mounting a separation instrument on the proximal end of the retractor before exposing the working channel to tissue along the retractor.

65. The method of claim 63, further comprising:

positioning a viewing element to view the location through the retractor.

66. The method of claim 63, wherein forming the working channel includes sequentially dilating tissue through the incision before inserting the distal end of the retractor.

67. The method of claim 63, wherein enlarging the working channel includes simultaneously laterally separating and pivoting the first and second portions of the retractor.

68. The method of claim 63, wherein the location is adjacent the spinal column of the patient.

69. The method of claim 63, wherein the working channel defines a substantially oval cross-section when enlarged.

70. A surgical method for accessing a location in a patient, comprising:

sequentially dilating tissue of the patient to the location;

placing a retractor through the sequentially dilated tissue to provide a substantially enclosed working channel to the location, the retractor having a length between a distal end and a proximal end thereof;

performing a first surgical procedure through the substantially enclosed working channel;

enlarging the working channel to expose the working channel to tissue along the length of the retractor by separating and pivoting each of a first portion and a second portion of the retractor relative to one another; and performing a second surgical procedure through the enlarged working channel.

71. The method of claim 70, wherein the location is adjacent the spinal column of the patient.

72. The method of claim 70, wherein the working channel has a substantially oval cross-section when enlarged.

73. The method of claim 70, wherein the working channel has a substantially circular cross-section when substantially enclosed.

74. The method of claim 70, wherein the working channel is enlarged by simultaneously separating and pivoting the first and second portions of the retractor.

75. The method of claim 70, further comprising positioning a viewing element over the retractor.

76. The method of claim 70, further comprising positioning a viewing element in the working channel.

* * * * *